(12) United States Patent
Han et al.

(10) Patent No.: US 10,215,704 B2
(45) Date of Patent: Feb. 26, 2019

(54) COMPUTED TOMOGRAPHY USING INTERSECTING VIEWS OF PLASMA USING OPTICAL EMISSION SPECTROSCOPY DURING PLASMA PROCESSING

(71) Applicant: Tokyo Electron Limited, Minato-ku, Tokyo (JP)

(72) Inventors: Taejoon Han, Clifton Park, NY (US); Daniel Morvay, Mechanicville, NY (US); Mirko Vukovic, Slingerlands, NY (US)

(73) Assignee: Tokyo Electron Limited, Tokyo (JP)

( * ) Notice: Subject to any disclaimer, the term of this patent is extended or adjusted under 35 U.S.C. 154(b) by 0 days.

(21) Appl. No.: 15/448,069

(22) Filed: Mar. 2, 2017

(65) Prior Publication Data

US 2018/0252650 A1    Sep. 6, 2018

(51) Int. Cl.
*G01J 3/30* (2006.01)
*G01N 21/73* (2006.01)
(Continued)

(52) U.S. Cl.
CPC .............. *G01N 21/73* (2013.01); *G01J 3/443* (2013.01); *G01N 21/68* (2013.01); *G06T 11/003* (2013.01);
(Continued)

(58) Field of Classification Search
CPC .......... G01N 21/73; G01N 2201/1293; G01N 21/31; G01N 2201/10; G01J 3/443;
(Continued)

(56) References Cited

U.S. PATENT DOCUMENTS

| 4,692,630 A | 9/1987 | Gogol |
| 5,353,790 A | 10/1994 | Jacques et al. |

(Continued)

FOREIGN PATENT DOCUMENTS

| JP | H04-303599 A | 10/1992 |
| JP | 10-261625 | 9/1998 |

(Continued)

OTHER PUBLICATIONS

International Patent Application No. PCT/US2014/063565, "International Search Report and Written Opinion," dated Jan. 29, 2015, International Filing Date Oct. 31, 2014.

(Continued)

*Primary Examiner* — Jamil Ahmed
(74) *Attorney, Agent, or Firm* — Oblon, McClelland, Maier & Neustadt, L.L.P.

(57) ABSTRACT

Described herein are technologies to facilitate computed tomographic techniques to help identifying chemical species during plasma processing of a substrate (e.g., semiconductor wafer) using optical emission spectroscopy (OES). More particularly, the technology described herein uses topographic techniques to spatially resolves emissions and absorptions in at least two-dimension space above the substrate during the plasma processing (e.g., etching) of the substrate. With some implementations utilize optical detectors positioned along multiple axes (e.g., two or more) to receive incident incoming optical spectra from the plasma chamber during the plasma processing (e.g., etching) of the substrate. Because of the multi-axes arrangement, the incident incoming optical spectra form an intersecting grid.

26 Claims, 7 Drawing Sheets

(51) Int. Cl.
*H01J 37/32* (2006.01)
*G06T 11/00* (2006.01)
*G01J 3/443* (2006.01)
*H01L 21/3065* (2006.01)
*H01L 21/67* (2006.01)
*G01N 21/68* (2006.01)
*G01N 21/17* (2006.01)

(52) U.S. Cl.
CPC .. *H01J 37/32422* (2013.01); *H01J 37/32972* (2013.01); *H01L 21/3065* (2013.01); *H01L 21/67069* (2013.01); *G01N 2021/1787* (2013.01); *G01N 2201/1293* (2013.01); *H01J 2237/334* (2013.01)

(58) Field of Classification Search
CPC .............. G06T 11/003; H01J 37/32422; H01J 37/32972; H01J 2237/334; H01L 21/306; H01L 21/3065; H01L 21/67069
See application file for complete search history.

(56) References Cited

U.S. PATENT DOCUMENTS

| | | | |
|---|---|---|---|
| 5,956,138 | A | 9/1999 | Slater |
| 6,201,628 | B1 | 3/2001 | Basiji et al. |
| 6,381,008 | B1 | 4/2002 | Branagh et al. |
| 6,958,484 | B2 | 10/2005 | Mitrovic |
| 7,241,397 | B2 | 7/2007 | Fink et al. |
| 7,591,923 | B2 | 9/2009 | Mitrovic et al. |
| 8,416,509 | B2 | 4/2013 | Yi et al. |
| 8,513,583 | B2 | 8/2013 | Corke et al. |
| 8,553,218 | B2 | 10/2013 | Tinnemans et al. |
| 2003/0174325 | A1 | 9/2003 | Zhang et al. |
| 2004/0026035 | A1* | 2/2004 | Mitrovic .................. G01J 3/443 156/345.24 |
| 2004/0104681 | A1 | 6/2004 | Mitrovic |
| 2009/0251700 | A1 | 10/2009 | Venugopal et al. |
| 2011/0013175 | A1 | 1/2011 | Davis et al. |
| 2013/0141720 | A1 | 6/2013 | Park et al. |
| 2015/0124250 | A1* | 5/2015 | Bao .......................... G01J 3/443 356/316 |

FOREIGN PATENT DOCUMENTS

| | | |
|---|---|---|
| JP | 2005-328050 A | 11/2005 |
| JP | 2008-199014 A | 8/2008 |
| JP | 2013-021321 A | 1/2013 |
| WO | WO 2013/029957 A2 | 3/2013 |
| WO | WO 2013/095776 A1 | 6/2013 |

OTHER PUBLICATIONS

Office Action dated Mar. 14, 2017 in corresponding JP Patent Application No. 2016-527330 (with English translation); 10 pgs.
Office Action dated May 23, 2017, in Korean Patent Application No. 10-2016-7014192 (w/English-language translation).
Kagaku Jiten, Japan, Tokyo Kagaku Dojin, Oct. 1, 1994, $1^{st}$ edition, p. 505.
International Search Report and Written Opinion dated Dec. 7, 2018 in Application No. PCT/US2018/041637.

* cited by examiner

COMPUTED TOMOGRAPHY USING INTERSECTING VIEWS OF PLASMA USING OPTICAL EMISSION SPECTROSCOPY DURING PLASMA PROCESSING

BACKGROUND OF THE INVENTION

Often, the production of semiconductor devices, displays, photovoltaics, etc. involves, for example, plasma etching. Plasma etching is a form of plasma processing of semiconductor material and is often used to fabricate integrated circuits. Plasma etching typically involves the generation of a glow discharge (i.e., plasma) by application of radio-frequency or microwave power in means familiar to one skilled in the art. Ions, neutral and exited atoms from the plasma are applied to the wafer.

During the process, the plasma generates volatile etch products from the chemical reactions between the elements of the material etched and the reactive species generated by the plasma.

In plasma processing, the chemistry of the plasma strongly affects the processing rate. This is particularly true about the local chemistry of the plasma. The local chemistry of the plasma is the local concentrations of various chemical species in the plasma environment proximate the substrate being processed. Certain species, particularly transient chemical species, such as radicals have a great influence on the plasma processing outcome. It is known that elevated local concentrations of these species can produce areas of faster or slower processing, which may lead to inconsistencies in the production and ultimately in the devices being produced.

The chemistry of a plasma process is controlled in a direct or indirect manner through the control of a large number of process variables. Examples of such variables includes one or more RF or microwave powers supplied to excite the plasma, the gas flows and kinds of gases supplied to the plasma processing chamber, the pressure in the plasma processing chamber, the type of substrate being processed, the pumping speed delivered to the plasma processing chamber, and many more.

Optical emission spectroscopy (OES) has proven itself as a useful tool for process development and monitoring in plasma processing. In OES, the presence and concentrations of certain chemical species of particular interest, such as radicals, is deduced from acquired optical (i.e. light) emission spectra of the plasma, wherein the intensities of certain spectral lines and ratios thereof correlate to the concentrations of chemical species.

OES is usually done by acquiring optical emission spectra from a single elongated volume (i.e., "ray") within the plasma that is inside the plasma processing chamber. The collection of the optical emission signals inherently results in averaging of the plasma optical emission spectra along the length of this elongated volume and thus all the information about local variations of the plasma optical emission spectra. As a result, all local variations of chemical species concentrations are generally lost.

BRIEF DESCRIPTION OF THE DRAWINGS

The Detailed Description references the accompanying figures. In the figures, the left-most digit(s) of a reference number identifies the figure in which the reference number first appears. The same numbers are used throughout the drawings to reference like features and components.

DETAILED DESCRIPTION

Described herein are technologies to facilitate computed tomographic techniques to help identifying chemical species during plasma processing of a substrate (e.g., semiconductor wafer) using optical emission spectroscopy (OES). More particularly, the technology described herein spatially resolves emissions and absorptions in at least two-dimension space above the substrate during the plasma processing (e.g., etching) of the substrate.

More particularly still, the technology described herein utilizes optical detectors positioned along multiple axes (e.g., two or more) to receive incident incoming optical spectra from the plasma chamber during the plasma processing (e.g., etching) of the substrate. Because of the multi-axes arrangement, the incident incoming optical spectra form an intersecting grid (e.g., "detector grid").

The detector grid establishes zones of interaction within the etch chamber and immediately above the surface of the substrate. Using these zones, embodiments of the technology described herein may determine chemical species within each zone. Herein, this is called localized determination, determining localized chemical species, or the like.

Using input from the optical detectors that are arranged along multiple axes to form the detection grid, an embodiment described herein monitors zones of interaction within the OES spectra being observed in the etch chamber during the plasma processing (e.g., etching) of the substrate. With these zones, the embodiment localizes and pinpoints locations for the found chemical compositions within the etch chamber.

One or more of the embodiments described herein utilize computed tomographic techniques to localize and pinpoint locations of the found chemical compositions. Generally, computed tomography techniques include those that facilitate imaging, mapping, or tracking of a volume by sections through the use of penetrating or emerging energy (e.g., X-ray, ultrasound, and the like) Often, it is based on the mathematical procedure called computed tomographic reconstruction.

Example Plasma Processing Systems

In the development of plasma processes, it is useful to know the two-dimensional distribution of chemical species of interest above the surface of the substrate being processed. With this knowledge, changes in the system design and/or process parameters can be made to minimize variations of the processing outcome across the substrate.

In addition, a detection of an abrupt change in particular chemical species in the plasma can signal the end of a plasma processing step (i.e., endpoint). For example, a detection of a chemical species than the one that was being etched on the substrate may indicate that the etching process is complete. Ability to determine the plasma processing step endpoint across the entire surface of the substrate leads to improved device yields. This is because the processing step does not end prematurely.

Figure 1A:
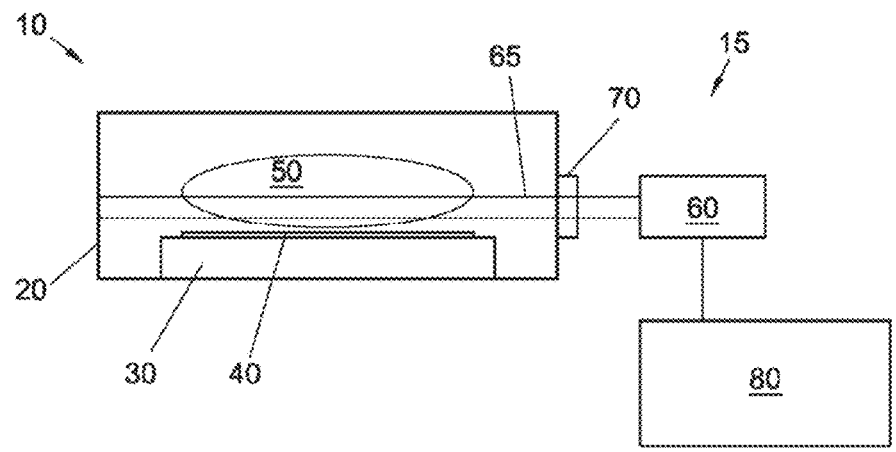
FIGS. 1A and 1B illustrate two views of an example plasma processing system in accordance with the technology described herein.
Figure 1B:
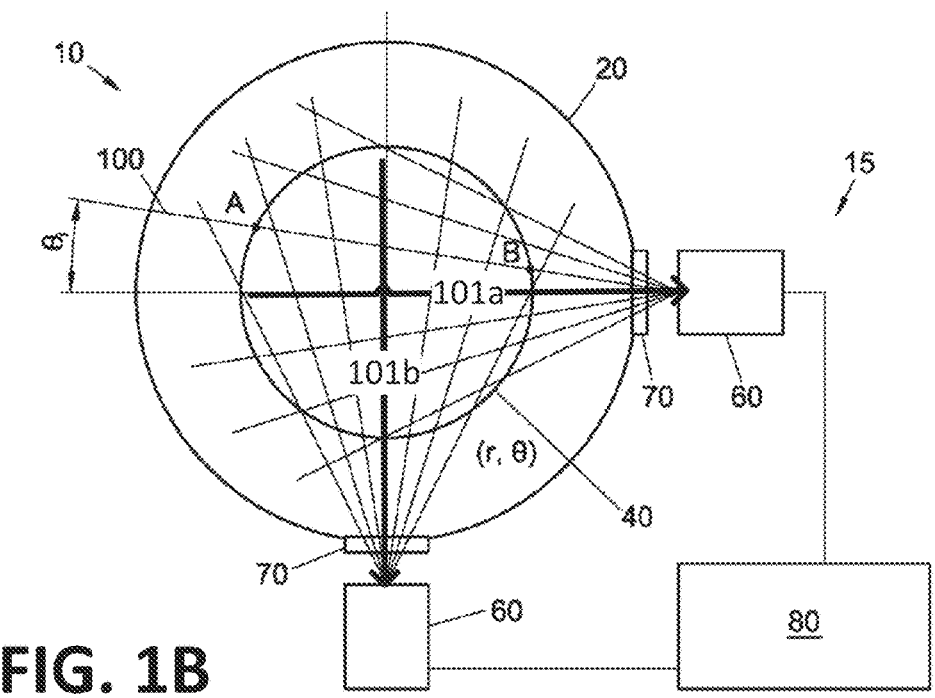

FIGS. 1A and 1B show an example of a plasma processing system 10 suitable for use with an embodiment of the technology described herein. The plasma processing system 10 is equipped with a plasma optical emission spectroscopy (OES) system 15. Plasma processing system 10 includes plasma processing chamber 20, inside which a substrate holder 30 is disposed for receiving a substrate 40 to be processed. An electrostatic chuck is an example of the substrate holder 30.

Although not shown, radio frequency (RF) and/or microwave power is supplied to the plasma processing chamber 20 to ignite and sustain a plasma 50 proximate the substrate 40. The energetic chemical species from the plasma 50 are used to perform a plasma processing step on substrate 40. Processing gasses are flowed into the plasma processing chamber 20 and a pumping system (not shown) maintains a vacuum in the plasma processing chamber 20, at the desired process pressure. Examples of plasma processing steps include plasma etching, plasma-enhanced chemical vapor deposition (PECVD), plasma-enhanced atomic layer deposition (PEALD), etc. The technology described herein are applicable to any kind of plasma processing.

The plasma OES system 15 is used to acquire plasma optical emission spectra via at least one optical detector 60. This optical detector has at least one spectrometer (not shown) to actually acquire the optical emission spectra from the plasma in the plasma processing chamber 20. The optical detector 60 communicates the acquired optical emission spectra to and is controlled by controller 80. Controller 80 may be a special-purpose computer or a specially programmed general-purpose computer. That computer may be located proximate to plasma processing system 10 or may be located remotely, and connected via an intranet or internet connection to the optical detector 60.

The spectrometer of the optical detector 60 has optics configured in such a way that it collects plasma optical emissions from a shallow volume 65 of space within the plasma 50 and immediately above the surface of the substrate 40. Herein, this volume may also be called a "ray" 65.

With the cross-section view of FIG. 1A, only one ray 65 is seen traversing the plasma 50 located within the plasma processing chamber 20, proximate substrate 40 being processed. The ray is a pencil-shaped portion of space from which the optical emission spectra are collected. The collected spectra represent an integral of contributions to the collected plasma optical emission spectrum from all points located along and within the ray 65.

In a typical configuration, the ray 65 is oriented substantially parallel with the surface of the substrate 40 and is maintained at a small distance from the surface of substrate 40, so as to reduce optical interference from the substrate surface, yet is kept close enough to the substrate 40 to sample the plasma chemistry proximate the substrate surface.

Optical access to the plasma processing chamber 20 is typically provided by optical window 70. Optical window 70 includes a translucent or transparent material such as glass, quartz, fused silica, sapphire, or the like. The specific material is chosen depending on the application and how aggressive the chemistry of the plasma 50 is.

As it names implies, controller 80 controls the plasma optical emission spectroscopy (OES) system 15. Controller 80 also computes the plasma optical distribution as a function of spatial location, wavelength, and intensity. Controller 80 also computes the spatial distribution of chemical species of interest from the computed plasma optical distribution. This information can then be used for process development, plasma processing tool development, in-situ plasma process monitoring, plasma process fault detection, plasma process endpoint detection, etc.

FIG. 1B shows the top schematic view of the plasma processing system 10. As depicted, system 10 has multiple rays 100 being used to sample the plasma emission spectra, which is in accordance with at least one embodiment of the technology described herein.

The plasma processing system 10 of FIG. 1B has two optical detectors 60 that positioned in multi-axes arrangement so that their rays intersect. As depicted, each optical detector 60 has seven spectrometers (not shown) matching seven rays 100, as depicted. Of course, other implementations have more spectrometers (e.g., 50, 100, 128, 256, 1048, 2000, or more).

The spectrometers of each optical detector are arranged and positioned so that their rays (or rays 100) are non-coincident to the other spectrometers of that same optical detector. The spectrometers of each optical detector arranged so that the largest amount of spatial information is acquired from the plasma 50 above substrate 40. The number spectrometers (and thus rays) per optical detector 60 depends on the implementations particulars. In some implementations, there may be 128 rays (and spectrometers) or more per optical spectrometer.

The angle of each ray 100 is defined with respect to the centerline of its optical detector 60, as $\theta i$. Every point within the plasma processing chamber 20 can be defined by its polar coordinates, i.e. $(r, \theta)$, as shown in FIG. 1B.

Each optical detector has a central axis, which represents the line-of-sight view for that optical detector. Arrow 101*a* represents a first line-of-sight view for the optical detector facing the plasma processing chamber 20. Arrow 101*b* represents a second line-of-sight view for the other optical detector facing the plasma processing chamber 20.

Figure 2:
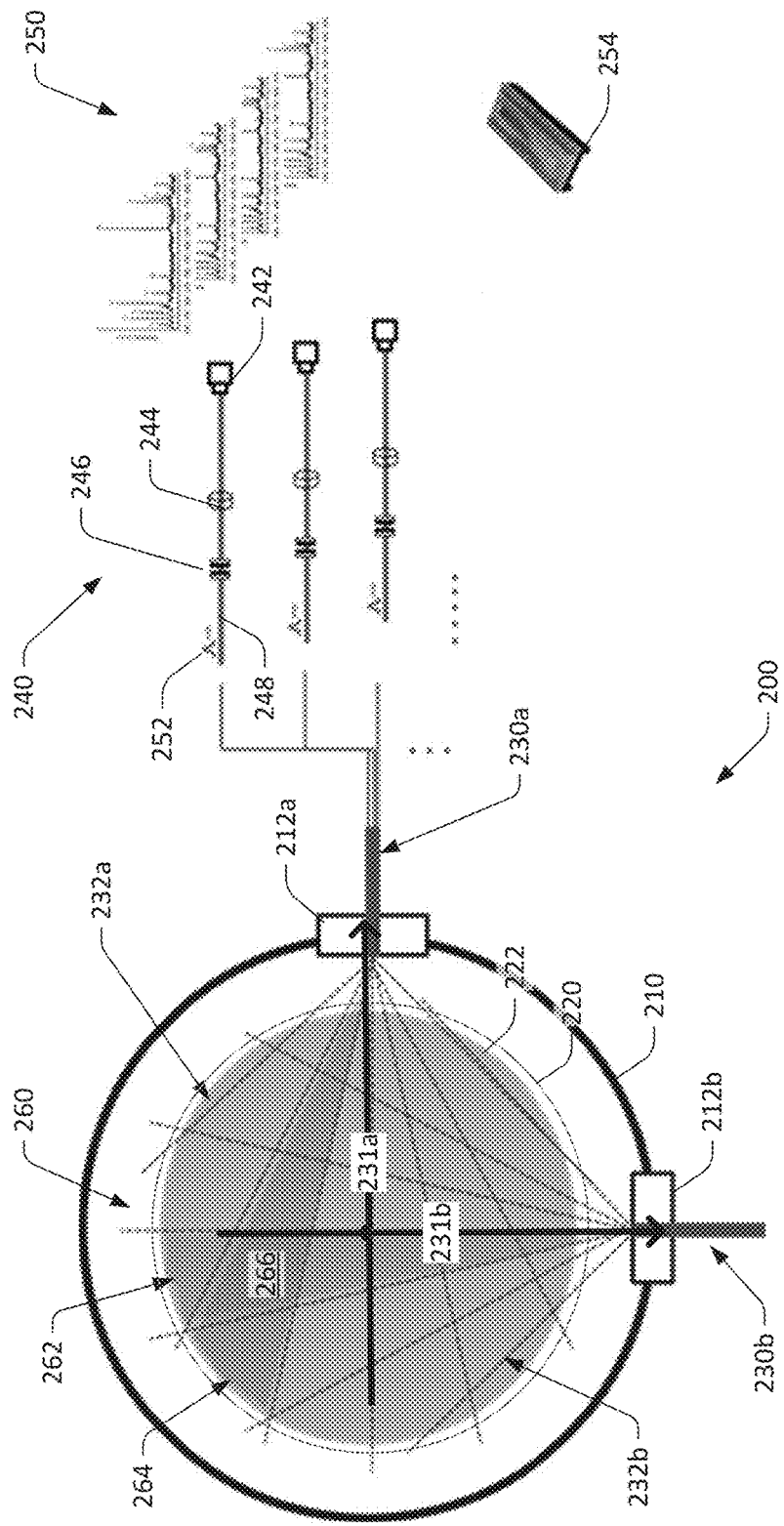
FIG. 2 illustrates a simplified depiction of another example plasma processing system in accordance with the technology described herein.

FIG. 2 shows a simplified depiction of an example of a plasma processing system 200 suitable for use with an embodiment of the technology described herein. Plasma processing system 200 includes a plasma processing chamber 210 with two small translucent windows 212*a*, 212*b* providing views therein the chamber. A substrate holder 220 is disposed inside the plasma processing chamber 210 for receiving a substrate 222 to be processed. An electrostatic chuck is an example of the substrate holder 220.

Although not shown fully, the plasma processing system 200 is equipped with a plasma OES system with similar components and operation as the system 15 described above. Differences between that system 15 and the plasma OES system of this embodiment are depicted in FIG. 2 and described herein.

The plasma OES system includes two optical detectors 230*a*, 230*b*, one optical detector per window (e.g., 212*a*, 212*b*). An optical detector includes multiple spectrometers. For example, optical detector 230*a* includes an example spectrometer 240. Depending upon the embodiment, light may be transmitted to the spectrometers using a waveguide 248 from the window (e.g., window 212*a*) or direct connection to the plasma processing chamber 210.

The example spectrometer 240 includes a single high sensitivity photodiode 242 with lens 244, and optical filters

246. This example spectrometer 240 (and other embodiments) may include or utilize a photodiode array 254, an interferometer using a grating or a prism, a photomultiplier tube (PMT), and/or an array of PMTs.

In some implementations, the spectra 252 (e.g., light) travels down the waveguide 248 and passes through a filter 246 that separates the incoming spectra into particular bands of wavelengths. This is depicted by graphs 250. The light may also pass through an interferometer (i.e., a beam splitter or light dispersion unit) or PMTs. Examples of suitable interferometers include prisms and tightly spaced grating. The light is focused by a lens 244 and detected by a photodiode 242 (or photodiode array 254) or other photodetectors. The waveguide 248 may utilize fiber optics.

By separating the incoming spectra into particular bands of wavelengths (e.g., see 250), the system can identify particular colors and associate those colors with individual chemical species in the plasma. In other implementations, a charge coupled device (CCD) may be employed to filter and/or detect the incoming spectra of various particular wavelength bands. In other implementations, an array of photodetectors may be employed with each spaced to receive a split beam of the spectrum of incoming light.

The spectrometers of each optical detector 230*a*, 230*b* are arranged and positioned in a manner so that their rays, 232*b* form a fan the encompasses the largest amount of spatial information that can be acquired from the plasma 50 above substrate 40. The spectrometers of each optical detector.

In some implementations, the spectrometers are arranged with an equal amount of angular separation between each ray. Also, in some implementations, the range of the fan of the rays includes at least the volume/area above the surface of the substrate. In some implementations, the angular separation may not be equal. In some implementations, the range of the fan of rays may include volume outside the perimeter of the substrate.

As depicted, the optical detectors 230*a*, 230*b* are positioned orthogonally relative to each other. That is, the central axis of each optical detector is orthogonal relative to the central axis of the other. More generally, this and other embodiments may be described as intersecting multi-axis optical detectors. That is, the central axes of the optical detectors are arranged and positioned so that their associated rays intersect each other. Alternatively, still, this arrangement may be described as multiple optical detectors where each detector has spectrometers with rays that intersect the rays of one or more spectrometers of other optical detectors.

The number spectrometers (and thus rays) per optical detector 230*a*, 230*b* depends on the implementation particulars. In some implementations, there may be 128 rays (and spectrometers) or more per optical spectrometer. In some implementations, there may be over a thousand rays (and spectrometers) or more per optical spectrometer. The greater the number of spectrometers the greater the spatial resolution.

Using the example plasma processing system 200, computed tomographic techniques may generate a determination of the chemical species in each zone. The particulars of the computed tomographic techniques are discussed later.

In short, the plasma OES system maps a shallow volume immediately above the substrate 222 as a computed tomographic volume 260. Based on OES information obtained from the appropriate spectrometers of optical detector 230*b*, the system identifies the chemical species in slice 262 of computed tomographic volume 260 based upon spectra input. Similarly, based on OES information obtained from the appropriate spectrometers of optical detector 230*a*, the system identifies the chemical species in slice 264 of computed tomographic volume 260 based upon spectra input. Armed with the knowledge of the physical arrangement of the spectrometers that obtained the spectra input, the system uses computed tomographic techniques to calculate/determine/specify a spatial zone (e.g., zone 266) where the chemical species occur in the plasma.

Based on the optical emissions within the plasma processing chamber 210, a system can determine a chemical species in the plasma by utilizing optical emission spectra (OES) where the light collected from the plasma processing chamber 210 is broken down into individual wavelengths. These wavelengths represent the various chemical species found within the plasma and the plasma processing chamber 210. Conventionally, OES observes the complete plasma processing chamber 210 as a single entity, averaging all collected light representing averaged chemical compositions Each optical detector has a central axis, which represents the line-of-sight view for that optical detector. Arrow 231*a* represents a first light-of-sight view for the optical detector 230*a* facing the plasma processing chamber 210. Arrow 231*b* represents a second light-of-sight view for the optical detector 230*b* facing the plasma processing chamber 210.

Figure 3:
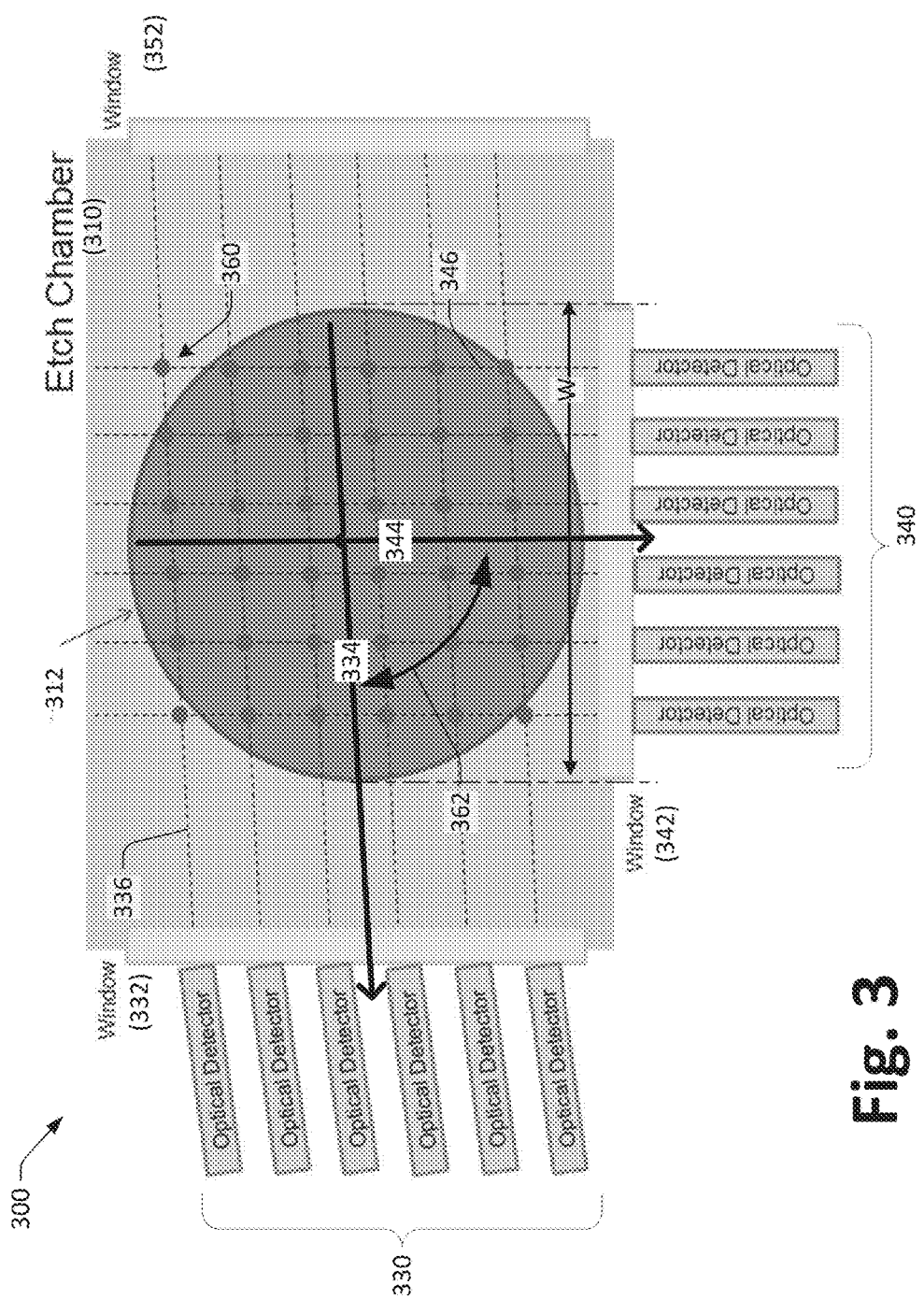
FIGS. 3-5 illustrate three different examples of plasma processing systems in accordance with the technology described herein.

FIG. 3 shows another example of plasma optical emission spectrographic (OES) system 300 that represents another embodiment of the technology described herein. For the sake of simplicity, only portions of the overall system are depicted.

As shown, the system 300 includes an etch chamber 310 with a substrate 312 therein. The system 300 also includes at least two arrays of multiple mutually parallel OES optical detectors.

A first array 330 of multiple mutually parallel OES optical detectors is positioned to receive optical input through window 332. The first array 330 is configured to have a first line-of-sight view 334 of the plasma over the substrate 312 on a substrate holder in the etch chamber 310 of a plasma processing system. Each optical detector of the first array 330 has at least one ray (e.g., 336) that is co-axial with its optical detector.

A second array 340 of multiple mutually parallel OES optical detectors is positioned to receive optical input through window 342. The second array 340 is configured to have a second line-of-sight view 344 of the plasma over the substrate 312 on the substrate holder in the etch chamber 310 of the plasma processing system. Each optical detector of the second array 340 has at least one ray (e.g., 346) that is co-axial with its optical detector.

The OES optical detectors of each array are described as "mutually parallel." Herein, optical detectors are mutually parallel when a central axis of each OES optical detector of a particular array is configured in parallel alignment with the other optical detectors of the same array. That is, a ray along the central axis of each optical detector of each array does not intersect the central-axis ray of another detector of that array.

Relative to each other, the first line-of-sight view 334 and second line-of-sight view 344 intersect within the etch chamber. Indeed, they intersect within the plasma and over the substrate 312. The line-of-sight views are non-coextensive. That is, they are not co-axial to each other. Since the line-of-sight views intersect, they are non-parallel. The rays of these line-of-sight views also intersect. Point 360 is an example intersection point of ray 336 and ray 346.

In addition, the first line-of-sight view 334 and second line-of-sight view 344 are non-orthogonal relative to each other. That is, they are not at right angles to each other. As depicted in FIG. 3, with some implementations, the angle 362 between the line-of-sight views is acute (between 0 and 90 degrees). In some implementations, the angle 362 between the line-of-sight views is obtuse (between 90 and 180 degrees).

The system 300 has a first viewport (e.g., window 332) that is designed to provide the first line-of-sight view 334 to the etch chamber for the first array 330 of multiple OES optical detectors. Similarly, the system 300 has a second viewport (e.g., window 342) designed to provide the second line-of-sight view 344 to the etch chamber for the second array 340 of multiple OES optical detectors. Since the optical detectors are mounted outside the etch chamber 310, the viewports must necessarily be at least translucent (i.e., allowing at least some light to pass therethrough). In some implementations, the viewports are transparent or clear.

Unlike that windows/viewports shown with systems 10 and 200, the windows/viewports are significantly wider. Indeed, with some implementations, at least one of the viewports has a width at least as wide (W) as a width of the substrate holder and/or of the substrate 312 itself.

In the alternative, there may be one contiguous window shared by both arrays (330 and 340) of optical detectors in a manner that allows for intersecting line-of-sight views of the plasma in the etch chamber 310. In another alternative, the arrays of optical detectors may be mounted inside the etch chamber. In this scenario, no viewport is needed. A window 352 is shown, but it has no accompanying array of optical detectors.

Figure 4:
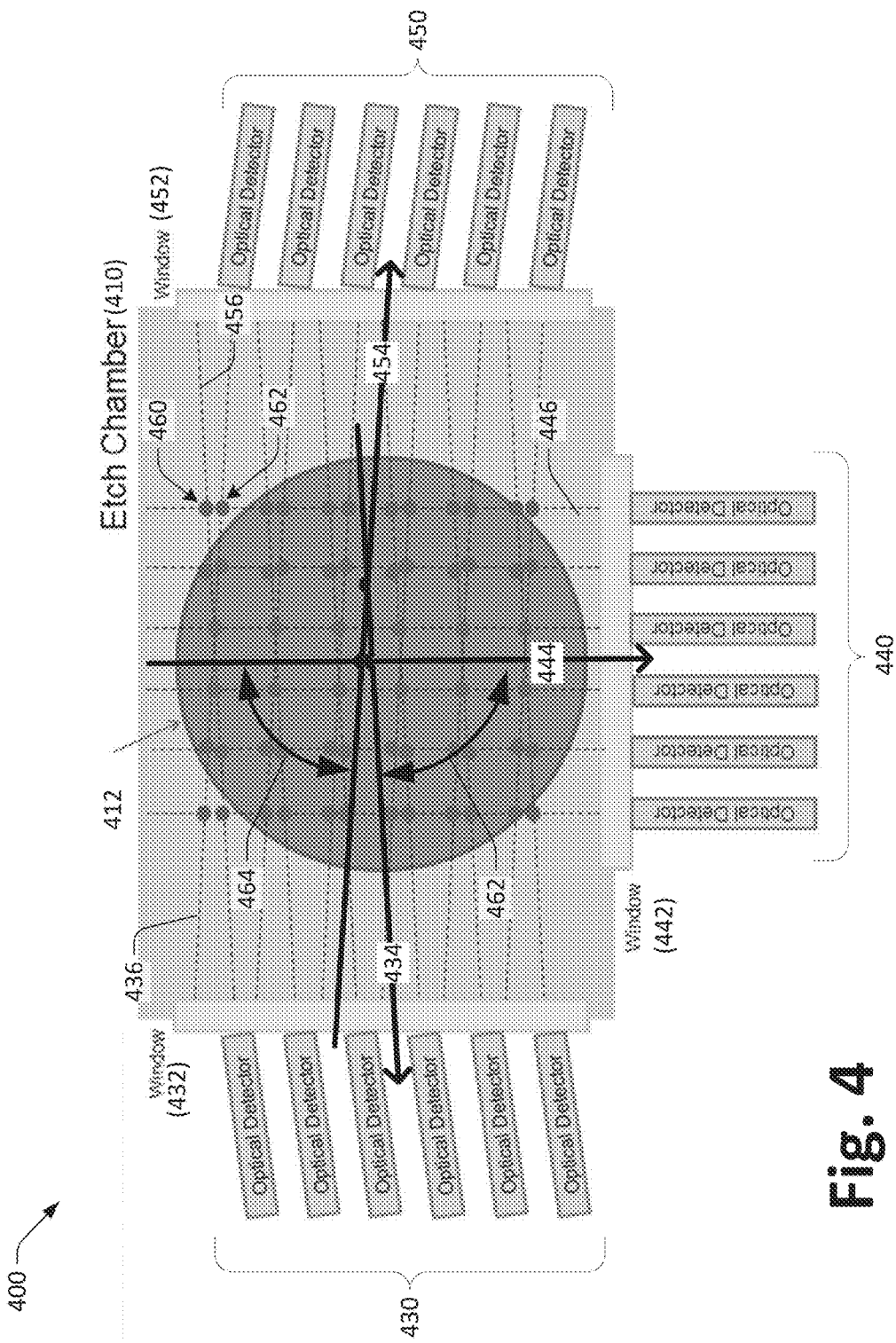

FIG. 4 shows another example of plasma optical emission spectrographic (OES) system 400 that represents another embodiment of the technology described herein. For the sake of simplicity, only portions of the overall system are depicted. System 400 is much like system 300. The key difference is that an additional (i.e., third) array of optical detectors is added. So, there are three arrays of optical detectors being used with this system.

As shown, the system 400 includes an etch chamber 410 with a substrate 412 therein. The system 400 also includes at least three arrays of multiple mutually parallel OES optical detectors.

A first array 430 of multiple mutually parallel OES optical detectors is positioned to receive optical input through window 432. The first array 430 is configured to have a first line-of-sight view 434 of the plasma over the substrate 412 on a substrate holder in the etch chamber 410 of a plasma processing system. Each optical detector of the first array 430 has at least one ray (e.g., 436) that is co-axial with its optical detector.

A second array 440 of multiple mutually parallel OES optical detectors is positioned to receive optical input through window 442. The second array 440 is configured to have a second line-of-sight view 444 of the plasma over the substrate 412 on the substrate holder in the etch chamber 410 of the plasma processing system. Each optical detector of the second array 440 has at least one ray (e.g., 446) that is co-axial with its optical detector.

A third array 450 of multiple mutually parallel OES optical detectors is positioned to receive optical input through window 452. The third array 450 is configured to have a third line-of-sight view 454 of the plasma over the substrate 412 on the substrate holder in the etch chamber 410 of the plasma processing system. Each optical detector of the third array 450 has at least one ray (e.g., 456) that is co-axial with its optical detector.

Relative to each other, the first line-of-sight view 434, second line-of-sight view 444, and third line-of-sight view 454 intersect within the etch chamber. Indeed, they intersect within the plasma and over the substrate 412. The line-of-sight views are non-coextensive. That is, they are not co-axial to each other. Since the line-of-sight views intersect, they are non-parallel. The rays of these line-of-sight views also intersect. Point 460 is an example intersection point of ray 436 and ray 446. And point 462 is an example intersection point of ray 446 and ray 456.

In addition, the first line-of-sight view 434, second line-of-sight view 444, and third line-of-sight view 454 are non-orthogonal relative to each other. That is, they are not at right angles to each other. As depicted in FIG. 4, with some implementations, the angle (e.g., 462 and 464) between a pair of the line-of-sight views is acute (between 0 and 90 degrees). In some implementations, the angle 462 between a pair of the line-of-sight view is obtuse (between 90 and 180 degrees).

The system 400 has a first viewport (e.g., window 432) that is designed to provide the first line-of-sight view 434 to the etch chamber for the first array 430 of multiple OES optical detectors. Similarly, the system 400 has a second viewport (e.g., window 442) designed to provide the second line-of-sight view 444 to the etch chamber for the second array 440 of multiple OES optical detectors. A third viewport (e.g., window 452) designed to provide the third line-of-sight view 454 to the etch chamber for the second array 450 of multiple OES optical detectors.

Figure 5:
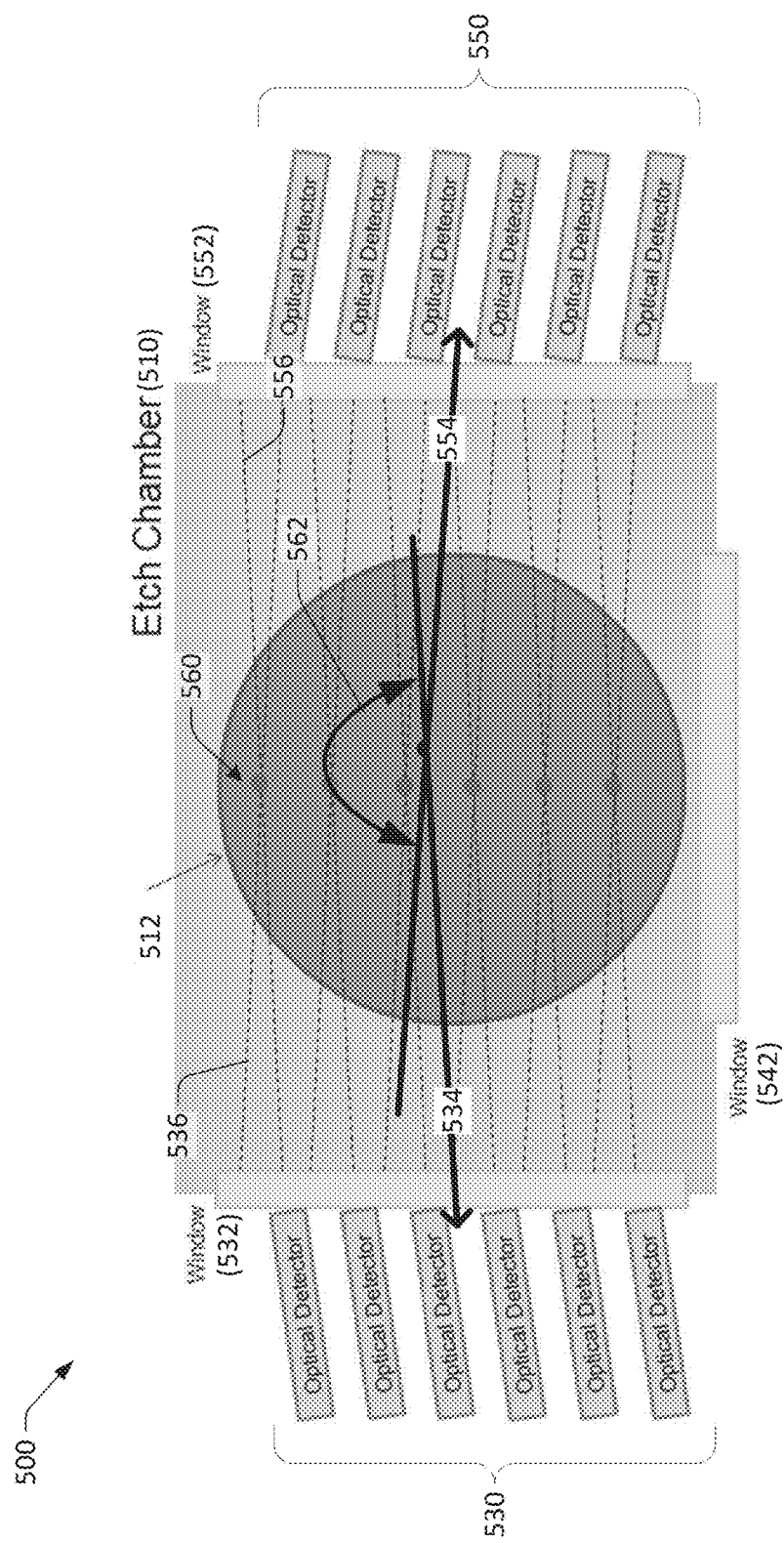

FIG. 5 shows another example of plasma optical emission spectrographic (OES) system 500 that represents another embodiment of the technology described herein. For the sake of simplicity, only portions of the overall system are depicted. System 500 is much like system 400. The key difference is that one of the three arrays of optical detectors is removed. So, there are only two arrays of optical detectors being used with this system.

As shown, the system 500 includes an etch chamber 510 with a substrate 512 therein. The system 500 also includes at least three arrays of multiple mutually parallel OES optical detectors.

A first array 530 of multiple mutually parallel OES optical detectors is positioned to receive optical input through window 532. The first array 530 is configured to have a first line-of-sight view 534 of the plasma over the substrate 512 on a substrate holder in the etch chamber 510 of a plasma processing system. Each optical detector of the first array 530 has at least one ray (e.g., 536) that is co-axial with its optical detector.

For the sake of consistency in terms, the second of two arrays is called the "third array." This is only to aid in readability. It is not intended to limit claim interpretation.

The third array 550 of multiple mutually parallel OES optical detectors is positioned to receive optical input through window 552. The third array 550 is configured to have a third line-of-sight view 554 of the plasma over the substrate 512 on the substrate holder in the etch chamber 510 of the plasma processing system. Each optical detector of the third array 550 has at least one ray (e.g., 556) that is co-axial with its optical detector.

Relative to each other, the first line-of-sight view 534 and third line-of-sight view 554 intersect within the etch chamber. Indeed, they intersect within the plasma and over the substrate 512. The line-of-sight views are non-coextensive. That is, they are not co-axial to each other. Since the line-of-sight views intersect, they are non-parallel. The rays of these line-of-sight views also intersect. Point 560 is an example intersection point of ray 536 and ray 556.

In addition, the first line-of-sight view 534 and third line-of-sight view 554 are non-orthogonal relative to each other. That is, they are not at right angles to each other. As depicted in FIG. 5, with some implementations, the angle (e.g., 562) between a pair of the line-of-sight views is obtuse (between 90 and 180 degrees).

The system 500 has a first viewport (e.g., window 532) that is designed to provide the first line-of-sight view 534 to the etch chamber for the first array 530 of multiple OES optical detectors. Similarly, the system 500 has a third viewport (e.g., window 552) designed to provide the third line-of-sight view 554 to the etch chamber for the second array 550 of multiple OES optical detectors. Notice that the first and third windows (532 and 552) are directly across from each other. That is, they are facing each other. They are approximately 180 degrees from each other. As depicted, the angles of the line-of-sight views are not in alignment with the windows. Rather than being 180 degrees apart, the line-of-sight views are obtuse from each other. Because of this, the line-of-sight views intersect.

As depicted, each of the OES optical detectors of the systems 400, 400, and 500 includes one spectrometer. That spectrometer is configured to observe one ray from the etch chamber and that ray shares a common central axis with its optical detector. In other implementations, one or more of the optical detectors may have multiple spectrometers. Each spectrometer of each multi-spectrometer OES optical detector is configured to observe one ray from the etch chamber, and the rays do not intersect. In some implementations, the spectrometers of each multi-spectrometer OES optical detector collectively observe a fan of rays from the etch chamber.

Computed Tomography

The embodiments described herein utilize computed tomographic reconstruction techniques to localize and pinpoint locations of the found chemical compositions. Generally, computed tomography techniques include those that facilitate imaging, mapping, or tracking of a volume by sections using penetrating or emerging energy (e.g., X-ray, ultrasound, and the like) Often, it is based on the mathematical procedure called computed tomographic reconstruction.

With the embodiments described herein, a computed tomographic reconstruction of the plasma in the etch chamber of a plasma processing system is produced. Given the chemical species identified by the plasma OES system, the computed tomographic system determines the spatial locations of those identified chemical species.

Generally speaking, examples of the computed tomographic reconstruction techniques employ one or more main approaches (i.e., "CT reconstruction algorithms"). Those approaches use 1) using simultaneous linear equations, iteration, filtered backprojection, and/or Fourier reconstruction.

More particularly, other examples of computed tomographic reconstruction techniques that are employed include Maximum Likelihood Expectation Maximization (MLEM), Ordered Subsets Expectation Maximization (OSEM), One Step Late Maximum a Posteriori Expectation Maximization (OSL-MAPEM), Bayesian Reconstructions, and/or Abel Inversions. In some implementations, a Savitzky-Golay filter is applied to reduce the number of data points during processing.

Example Methodological Implementation

Figure 6:
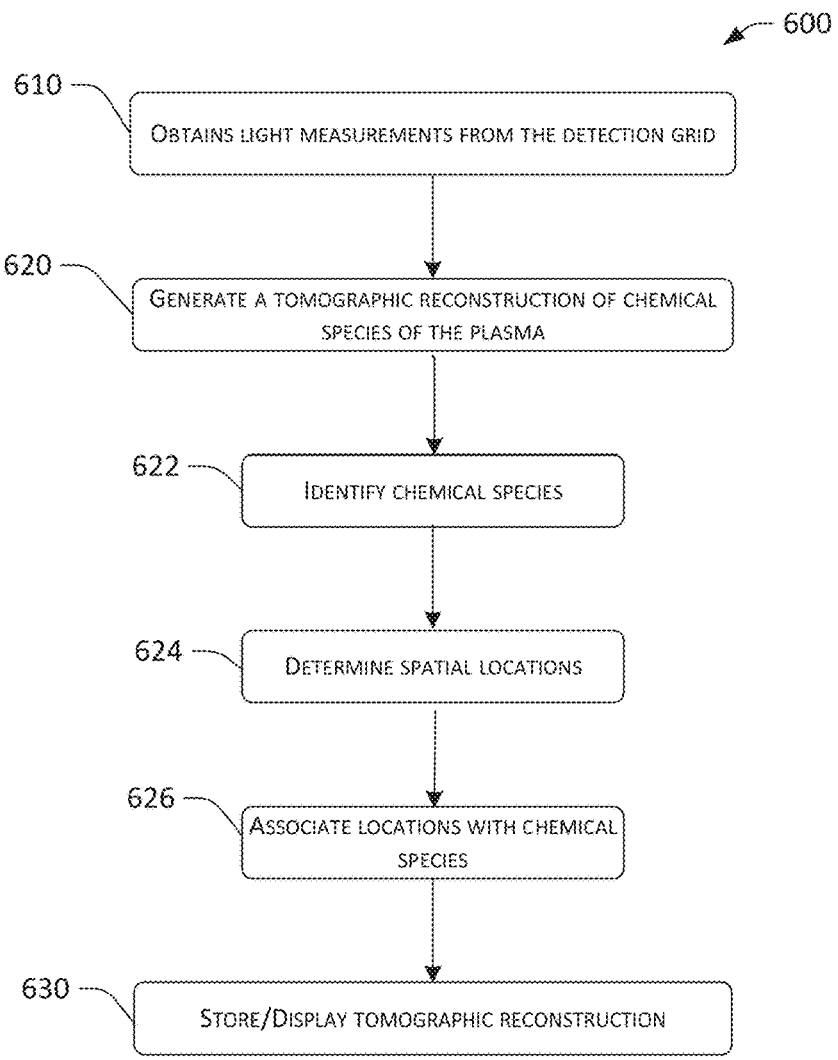
FIG. 6 is a flowchart of a methodological implementation of computed tomographic reconstruction in accordance with implementations described herein.

FIG. 6 shows an example process 600 illustrating the technology as described herein. The example process 600 may be implemented as part of computed tomographic reconstruction (TR) system. That system is part of or works in cooperation with a plasma OES system.

At block 610, a TR system obtains light measurements from the detection grid in the plasma. The detection grid is formed by the intersecting rays of a collection of optical detectors configured to receive incoming rays from plasma over a substrate on a substrate holder in an etch chamber of a plasma processing system. These measurements includes intensity of particular wavelengths and for particular bands of wavelengths.

At block 620, the TR system generates a computed tomographic reconstruction of chemical species of the plasma. The computed tomographic reconstruction includes chemical species identification (622), spatial location determination (624), and the association between the two (626). More specifically, the TR system identifies (622) the chemical species in the plasma based on the obtained light measurements. It also determines (624) the spatial locations of the identified chemical species in the plasma based on the obtained light measurements. With that information, the TR system associates (626) the determined locations in the plasma for one or more of the identified chemical species.

At block 630, the TR system stores the generated tomographic reconstruction. In addition or in the alternative, the TR system may display the generated tomographic reconstruction as cross-sections of the chemical species of the plasma. Other display options may be employed as well. For example, the computed tomographic reconstruction may be displayed as an isometric or other three-dimensional representation. In still another option, the computed tomographic representation may be presented in a virtual reality (VR) scenario.

Analytic and Discrete (Pixel-Based) Approach

Examples of the technology described herein may employ discrete approaches. That is, it may represent the measured data in a pixelized form.

Figure 7:
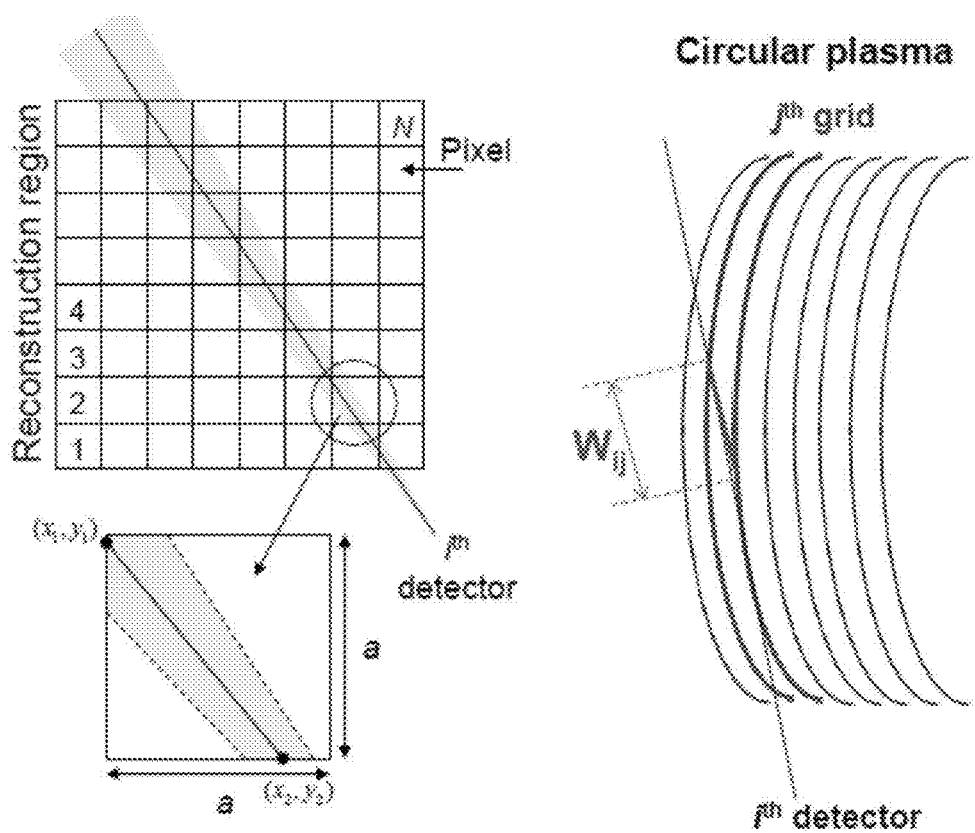
FIG. 7 illustrate additional details related to example implementations in accordance with implementations described herein.

FIG. 7 illustrates how a discrete approach may be accomplished. As illustrated:
- the geometry matrix (W), $w_{ij}$ is the contribution of the jth pixel to the ith detector;
- $f_i$ is the line-integrated data from ith detector;
- $g_i$ is intensity of jth pixel
- the inverse of W does not exist since the number of detectors is much smaller than that of pixels
- circular grids can be used for azimuthally symmetric plasma

ADDITIONAL AND ALTERNATIVE IMPLEMENTATION DETAILS

To facilitate a thorough understanding of the technology described herein and for purposes of explanation and not limitation, specific details are set forth, such as particular geometries of a plasma optical emission spectroscopy (OES) system, and descriptions of various components and processes. However, the invention may be practiced in other embodiments that depart from these specific details.

Herein, the term substrate represents the workpiece being processed. Unless the context indicates otherwise, examples of a substrate may include semiconductor wafer, liquid crystal display (LCD) panel, light-emitting diode (LED), photovoltaic (PV) device panel, etc.

Depending upon the embodiment, data collection may be continuous wave or pulsed. The results may be stored in a computer memory or discarded.

Depending upon the embodiment, spectrometers may include a single high sensitivity photodiode with optical filters, a photodiode array, an interferometer using a grating or a prism, a photomultiplier tube (PMT), or an array of PMTs.

Depending upon the embodiment, light may be transmitted using a waveguide or direct connection to/from the plasma etch chamber.

Depending upon the embodiment, signal processing could occur on a single computer, on an array of computes from a laptop to a computing cluster (supercomputer).

In some implementations, the light or spectra refer to only visible light. In other implementations, the light or spectra include non-visible light (e.g., infrared and ultraviolet). In still other implementations, the light or spectra include other electromagnetic waves or energy that is consistent with those emitted by chemical species being present in the plasma.

Reference herein to "one embodiment" or "an embodiment" refers to one or more features, structures, materials, or characteristics described at least one example embodiment of the technology described herein. It does not denote or imply that the features, structures, materials, or characteristics are present in every embodiment. Thus, the appearances of the phrases "in one embodiment" or "in an embodiment" in various places throughout this document are not necessarily referring to the same embodiment of the technology. Furthermore, the features, structures, materials, or characteristics may be combined in any suitable manner in one or more embodiments.

In the above description of example implementations, for purposes of explanation, specific numbers, materials configurations, and other details are set forth to explain better the present invention, as claimed. However, it will be apparent to one skilled in the art that the claimed invention may be practiced using different details than the example ones described herein. In other instances, well-known features are omitted or simplified to clarify the description of the example implementations.

The inventors intend the described example implementations to be primarily examples. The inventors do not intend these example implementations to limit the scope of the appended claims. Rather, the inventors have contemplated that the claimed invention might also be embodied and implemented in other ways, in conjunction with other present or future technologies.

Moreover, the word "example" is used herein to mean serving as an example, instance, or illustration. Any aspect or design described herein as "example" is not necessarily to be construed as preferred or advantageous over other aspects or designs. Rather, use of the word example is intended to present concepts and techniques in a concrete fashion. The term "techniques," for instance, may refer to one or more devices, apparatuses, systems, methods, articles of manufacture, and computer-readable instructions as indicated by the context described herein.

As used in this application, the term "or" is intended to mean an inclusive "or" rather than an exclusive "or." That is unless specified otherwise or clear from context, "X employs A or B" is intended to mean any of the natural inclusive permutations. That is if X employs A; X employs B; or X employs both A and B, then "X employs A or B" is satisfied under any of the preceding instances. Also, the articles "an" and "an" as used in this application and the appended claims should be construed to mean "one or more," unless specified otherwise or clear from context to be directed to a singular form.

These processes are illustrated as a collection of blocks in a logical flow graph, which represents a sequence of operations that can be implemented in mechanics alone or a combination of hardware, software, and firmware. In the context of software/firmware, the blocks represent instructions stored on one or more computer-readable storage media that, when executed by one or more processors, perform the recited operations.

Note that the order in which the processes are described is not intended to be construed as a limitation and any number of the described process blocks can be combined in any order to implement the processes or an alternate process. Additionally, individual blocks may be deleted from the processes without departing from the spirit and scope of the subject matter described herein.

The term "computer-readable media" is non-transitory computer-storage media. For example, non-transitory computer-storage media may include, but are not limited to, magnetic storage devices (e.g., hard disk, floppy disk, and magnetic strips), optical disks (e.g., compact disk (CD) and digital versatile disk (DVD)), smart cards, flash memory devices (e.g., thumb drive, stick, key drive, and SD cards), and volatile and non-volatile memory (e.g., random access memory (RAM), read-only memory (ROM)). Similarly, the term "machine-readable media" is non-transitory machine-storage media. Likewise, the term "processor-readable media" is non-transitory processor-storage media.

A non-transitory machine-readable storage medium can cause a machine to perform the functions or operations described, and includes any mechanism that stores information in a form accessible by a machine (e.g., computing device, electronic system, etc.), such as recordable/non-recordable media (e.g., read-only memory (ROM), random access memory (RAM), magnetic disk storage media, optical storage media, flash memory devices, etc.). A communication interface includes any mechanism that interfaces to any of a hardwired, wireless, optical, etc., medium to communicate to another device, such as a memory bus interface, a processor bus interface, an Internet connection, a disk controller, etc. The communication interface is configured by providing configuration parameters or sending signals to prepare the communication interface to provide a data signal describing the software content. The communication interface can be accessed via one or more commands or signals sent to the communication interface.

In the claims appended herein, the inventors invoke 35 U.S.C. § 112(f) only when the words "means for" or "steps for" are used in the claim. If such words are not used in a claim, then the inventors do not intend for the claim to be construed to cover the corresponding structure, material, or acts described herein (and equivalents thereof) in accordance with 35 U.S.C. 112(f).

A non-transitory machine-readable storage medium can cause a machine to perform the functions or operations described, and includes any mechanism that stores information in a form accessible by a machine (e.g., computing device, electronic system, etc.), such as recordable/non-recordable media (e.g., read-only memory (ROM), random access memory (RAM), magnetic disk storage media, optical storage media, flash memory devices, etc.). A communication interface includes any mechanism that interfaces to any of a hardwired, wireless, optical, etc., medium to communicate to another device, such as a memory bus interface, a processor bus interface, an Internet connection, a disk controller, etc. The communication interface is configured by providing configuration parameters or sending signals to prepare the communication interface to provide a

The invention claimed is:

1. A plasma optical emission spectrographic (OES) system comprising:
a first array of multiple OES optical detectors configured to have a first line-of-sight view of plasma over a substrate on a substrate holder in an etch chamber of a plasma processing system;
a second array of multiple OES optical detectors configured to have a second line-of-sight view of plasma in the etch chamber; and
circuitry configured to generate a computed tomographic reconstruction of chemical species of the plasma based on measurements received from the first array of multiple OES optical detectors and the second array of multiple OES optical detectors,
wherein, relative to each other, the first line-of-sight view and second line-of-sight view intersect within the etch chamber and are non-coextensive, non-parallel, and non-orthogonal,
wherein the generation of the computed tomographic reconstruction includes:
obtaining light measurements from light received from intersecting views of the first and second line-of-sight views;
identifying chemical species in the plasma based on the obtained light measurements;
determining spatial locations of the identified chemical species in the plasma based on the obtained light measurements;
associating the determined spatial locations in the plasma for one or more of the identified chemical species;
storing a tomographic reconstruction based on the association of the determined spatial locations in the plasma with the respective one or more of the identified chemical species.

2. A plasma OES system as recited in claim 1, wherein a central axis of each OES optical detector of a particular array is configured in parallel alignment with the other optical detectors of the same array.

3. A plasma OES system as recited in claim 1, wherein the first and second line-of-sight views are separated by an acute or an obtuse angle.

4. A plasma OES system as recited in claim 1, further comprising:
a first viewport configured to provide the first line-of-sight view to the etch chamber for the first array of multiple OES optical detectors;
a second viewport configured to provide the second line-of-sight view to the etch chamber for the second array of multiple OES optical detectors.

5. A plasma OES system as recited in claim 1, further comprising:
a first viewport configured to provide the first line-of-sight view to the etch chamber for the first array of multiple OES optical detectors;
a second viewport configured to provide the second line-of-sight view to the etch chamber for the second array of multiple OES optical detectors,
wherein the first and second viewport have a width at least as wide as a width of the substrate holder.

6. A plasma OES system as recited in claim 1, wherein each OES optical detector includes one spectrometer that is configured to observe one ray from the etch chamber, wherein the ray shares a common central axis with its optical detector.

7. A plasma OES system as recited in claim 1, wherein each OES optical detector includes multiple spectrometers, each spectrometer of each OES optical detector is configured to observe one ray from the etch chamber.

8. A plasma OES system as recited in claim 1, wherein each OES optical detector includes multiple spectrometers, wherein the spectrometers of each OES optical detector collectively observe a fan of rays from the etch chamber.

9. A plasma OES system as recited in claim 1, further comprising a third array of multiple OES optical detectors configured to have a third line-of-sight view of plasma in the etch chamber, wherein the third line-of-sight view intersects the first and second line-of-sight views within the etch chamber and the third line-of-sight view is non-coextensive, non-parallel, and non-orthogonal with either the first or second line-of-sight views.

10. A plasma OES system as recited in claim 1, further comprising:
a third array of multiple OES optical detectors configured to have a third line-of-sight view of plasma in the etch chamber, wherein the third line-of-sight view intersects the first and second line-of-sight views within the etch chamber and the third line-of-sight view is non-coextensive, non-parallel, and non-orthogonal with either the first or second line-of-sight views;
a third viewport configured to provide the third line-of-sight view to the etch chamber for the third array of multiple OES optical detectors.

11. A plasma OES system as recited in claim 1, wherein the substrate is a semiconductor wafer.

12. A plasma OES system as recited in claim 1, wherein at least one of the arrays includes at least one-hundred twenty-eight (128) OES optical detectors and/or wherein at least one of the OES optical detector includes at least one-hundred twenty-eight (128) OES spectrometers.

13. A computed tomography system for a plasma optical emission spectrography (OES), the system comprising:
a plasma OES subsystem that includes:
one or more first OES optical detectors configured to have a first line-of-sight view of plasma over a substrate on a substrate holder in an etch chamber of a plasma processing system;
one or more second OES optical detectors configured to have a second line-of-sight view of plasma in the etch chamber, wherein, relative to each other, the first line-of-sight view and second line-of-sight view intersect within the etch chamber;
a computed tomographic reconstruction system configured to generate a computed tomographic reconstruction of chemical species of the plasma, wherein the generation of the computed tomographic reconstruction includes:
obtaining light measurements from light received from intersecting views of the first and second line-of-sight views;
identifying chemical species in the plasma based on the obtained light measurements;
determining spatial locations of the identified chemical species in the plasma based on the obtained light measurements;
associating the determined spatial locations in the plasma for one or more of the identified chemical species; and storing a tomographic reconstruction based on the association of the determined spatial locations in the plasma with the respective one or more of the identified chemical species.

14. A plasma OES system as recited in claim 13, wherein, relative to each other, the first line-of-sight view and second line-of-sight view are non-coextensive, non-parallel, and non-orthogonal.

15. A plasma OES system as recited in claim 13, wherein the light measurements obtained includes intensity of light.

16. A plasma OES system as recited in claim 13, wherein the light measurements obtained includes light measurements for particular wavelengths of light or wherein the light measurements obtained includes light measurements for a particular band of wavelengths of light.

17. A plasma OES system as recited in claim 13, wherein:
multiple first OES optical detectors form a first array, wherein a central axis of each OES optical detector of the first array is configured in parallel alignment with the other optical detectors of the first array;
multiple second OES optical detectors form a second array, wherein a central axis of each OES optical detector of the second array is configured in parallel alignment with the other optical detectors of the second array.

18. A plasma OES system as recited in claim 13, wherein the first and second line-of-sight views are separated by an acute or an obtuse angle.

19. A plasma OES system as recited in claim 13 further comprising:
a first viewport configured to provide the first line-of-sight view to the etch chamber for the one or more first OES optical detectors; and
a second viewport configured to provide the second line-of-sight view to the etch chamber for the one or more second OES optical detectors.

20. A plasma OES system as recited in claim 13 further comprising:
a first viewport configured to provide the first line-of-sight view to the etch chamber for the one or more first OES optical detectors; and
a second viewport configured to provide the second line-of-sight view to the etch chamber for the one or more second OES optical detectors;
wherein the first and second viewport have a width at least as wide as a width of the substrate holder.

21. A plasma OES system as recited in claim 13, wherein each OES optical detector includes one spectrometer that is configured to observe one ray from the etch chamber, wherein the ray shares a common central axis with its optical detector; or
wherein each OES optical detector includes multiple spectrometers, each spectrometer of each OES optical detector is configured to observe one ray from the etch chamber; or
wherein each OES optical detector includes multiple spectrometers, wherein the spectrometers of each OES optical detector collectively observe a fan of rays from the etch chamber.

22. A plasma OES system as recited in claim 13, further comprising one or more third OES optical detectors configured to have a third line-of-sight view of plasma in the etch chamber, wherein the third line-of-sight view intersects the first and second line-of-sight views within the etch chamber and the third line-of-sight view is non-coextensive, non-parallel, and non-orthogonal with either the first or second line-of-sight views.

23. A plasma OES system as recited in claim 13, further comprising:
one or more third OES optical detectors configured to have a third line-of-sight view of plasma in the etch chamber, wherein the third line-of-sight view intersects the first and second line-of-sight views within the etch chamber and the third line-of-sight view is non-coextensive, non-parallel, and non-orthogonal with either the first or second line-of-sight views; and
a third viewport configured to provide the third line-of-sight view to the etch chamber for the one or more third OES optical detectors.

24. A method that facilitates computed tomographic reconstruction of plasma during plasma processing of a substrate in a plasma etch chamber of a plasma processing system, the method comprising:
obtaining light measurements from a collection of optical detectors configured to receive incoming rays from plasma over a substrate on a substrate holder in an etch chamber of a plasma processing system, wherein the rays form an intersecting grid within the plasma;
generating a computed tomographic reconstruction of chemical species of the plasma, wherein the generating includes:
identifying chemical species in the plasma based on the obtained light measurements;
determining spatial locations of the identified chemical species in the plasma based on the obtained light measurements; and
associating the determined spatial locations in the plasma for one or more of the identified chemical species; and
storing a tomographic reconstruction based on the association of the determined spatial locations in the plasma with the respective one or more of the identified chemical species.

25. The plasma OES system as recited in claim 1, wherein the generation of the computed tomographic reconstruction further includes applying a Savitzky-Golay filter to reduce a number of data points.

26. The plasma OES system as recited in claim 1, wherein the circuitry is configured to generate a three-dimensional representation of the one or more identified chemical species in the plasma based on the stored tomographic reconstruction.

* * * * *